US007476534B2

(12) United States Patent
Wismar

(10) Patent No.: US 7,476,534 B2
(45) Date of Patent: Jan. 13, 2009

(54) SOLID-STATE FERMENTER

(76) Inventor: Peter Lueth Wismar, Fischkaten 48, Wismar D-23970 (DE)

( * ) Notice: Subject to any disclaimer, the term of this patent is extended or adjusted under 35 U.S.C. 154(b) by 703 days.

(21) Appl. No.: 10/900,581

(22) Filed: Jul. 28, 2004

(65) Prior Publication Data

US 2005/0059141 A1    Mar. 17, 2005

(30) Foreign Application Priority Data

Jul. 31, 2003    (DE)    ................... 103 35 522

(51) Int. Cl.
*C12M 1/00*    (2006.01)
(52) U.S. Cl. .................................... 435/289.1
(58) Field of Classification Search ............ 435/289.1
See application file for complete search history.

(56) References Cited

U.S. PATENT DOCUMENTS

| | | | | |
|---|---|---|---|---|
| 5,595,910 | A | 1/1997 | Kant et al. ............ | 435/289.1 |
| 6,197,573 | B1 | 3/2001 | Suryanarayan et al. ... | 435/286.7 |
| 6,432,698 | B1 * | 8/2002 | Gaugler et al. ........... | 435/296.1 |
| 6,440,596 | B1 * | 8/2002 | Ruhl et al. ............... | 429/34 |
| 6,620,614 | B1 * | 9/2003 | Luth et al. ............... | 435/291.3 |

FOREIGN PATENT DOCUMENTS

| | | | |
|---|---|---|---|
| CA | 2384799 A1 * | 3/2001 | |
| DE | 44 06 632 C1 | 10/1995 | |
| EP | 0 683 815 B1 | 11/1995 | |
| FR | 2 583 059 | 12/1986 | |
| WO | WO 99/57239 | 11/1999 | |

OTHER PUBLICATIONS

M.V. Ramana Murthy, et al.; "Biochemical Engineering Aspects of Solid-State Fermentation"; Advances in Applied Microbiology, vol. 38, pp. 99-147.
D. Bahr, et al.; "Solid-State-Fermentation of Starter Cultures in Fluidized Bed"; BIOforum, vol. 18, 1995, pp. 16-21.
G. Saucedo-Castañeda, et al.; "Heat Transfer Simulation in Solid Substrate Fermentation"; Biotechnology and Bioengineering, vol. 35, 1990, pp. 802-808.

* cited by examiner

*Primary Examiner*—Walter D Griffin
*Assistant Examiner*—Lydia Edwards
(74) *Attorney, Agent, or Firm*—Norris McLaughlin & Marcus

(57) ABSTRACT

The invention relates to a solid-state fermenter for the cultivation of micro-organisms on solid substrates, in particular for large volumes. The filed of application of the invention is in the microbiological industry.

The solid-state fermenter according to the invention comprises one or more air-and water-permeable fermenter levels arranged on top of one another, connected with the wall of the container in such a way that neither air nor water can flow past laterally, with a culture substrate to be found on the fermenter levels for the micro-organisms to be cultivated, And wherein
   the cooling of the fermenter material is done by cooling lances rising vertically from the fermenter base and leading through the fermenter levels (4) and
   a seal (6) is installed between the fermenter levels (4), which is pressed against the inner wall of the fermenter by the mass of the level above it (4).

11 Claims, 3 Drawing Sheets

SOLID-STATE FERMENTER

FIELD OF THE INVENTION

The invention relates to a solid-state fermenter for the cultivation of micro-organisms on solid substrates, in particular for large volumes. The field of application of the invention is the microbiological industry.

BACKGROUND

WO 99/57239 has already manifested a solid-state fermenter comprising at least two fermenter levels permeable to air and water and arranged above one another, which are connected with the walls of the container in such a way that neither air nor water can flow past on the side, there being a culture substrate on the fermenter levels for the micro-organisms to be cultivated and a cooling device being fitted under each level.

In use, this fermenter manifests a number of disadvantages.

1. The use of a cooling system in the form of cooling spirals for each individual fermenter level, which run below the levels and each have to be provided with a flow of coolant and with a coolant discharge from the outside through the fermenter wall, results in a high risk of contamination of the fermenter material with the coolant used for cooling. This risk of contamination is in particular to be put down to the fact that each cooling spiral must be connected with the coolant feed and discharge tubes outside the fermenter with the help of 2 connectors (for feed and discharge of the coolant). Leaks can come about on these connectors. The risk of the occurrence of said leaks increases as the number of fermenter levels increases. As a result of the connection pieces of the cooling system protruding into the fermenter from the outside (one feed and one discharge per fermenter level), the insertion of the fermenter levels thereunder is connected with difficulties. In insertion, they must either be held at an angle or have been provided with a recess in order to be lowered past the connections and into the lower part of the fermenter.

2. A further problem with the solid state fermenter described under WO 99/57239 is that the fermenter levels are placed on "rings or otherwise shaped devices" (Claim 4). These "rings or otherwise shaped devices" are provided with a heat-stable gasket. This is to prevent water or air flowing past the fermenter levels. However, these "rings or otherwise shaped devices" have the effect that the insertion of the level underneath them is connected with difficulties.

Therefore, the invention was based on the task of eliminating the said disadvantages of the solid-state fermenter claimed in WO 99/57239 by constructive alterations and enabling the use of large volumes.

This task is solved according to the invention described below. The essential features of the invention area
  a new kind of cooling of the fermenter material and
  a new kind of sealing of the fermenter levels to the fermenter wall.

DESCRIPTION OF THE INVENTION

1. Cooling of the Fermenter Material

The cooling of the fermenter material is assured by cooling lances (FIGS. 1-3) rising vertically from the base of the fermenter. The distance of the cooling lances is based on the quantity of heat produced by the cultivated micro-organisms. The cooling lances are fitted in a triangular arrangement to one another (FIGS. 2a and 2b) with the result that each cooling lance manifests the same distance from the closest one. The cooling lances comprise an interior tube with a lower diameter, which is used for the return of the coolant, and a tube with a larger diameter, in which the first one is arranged centrally, which is used for the feeding of the coolant (FIG. 3). In the cross-section, the cooling lances display an annulus. The tube is provided with a circular cone shaped stopper at the upper end. Preferably, the interior tube ends open 1-2 cm in front of the stopper of the outer tube. The cooling lances have an outer diameter of preferably 1-3 cm. The ratio of the diameters of the two tubes to one another should preferably be designed in such a way that the flow velocity of the coolant in feeding is equal to the flow velocity of the coolant in the return.

Figure 1:
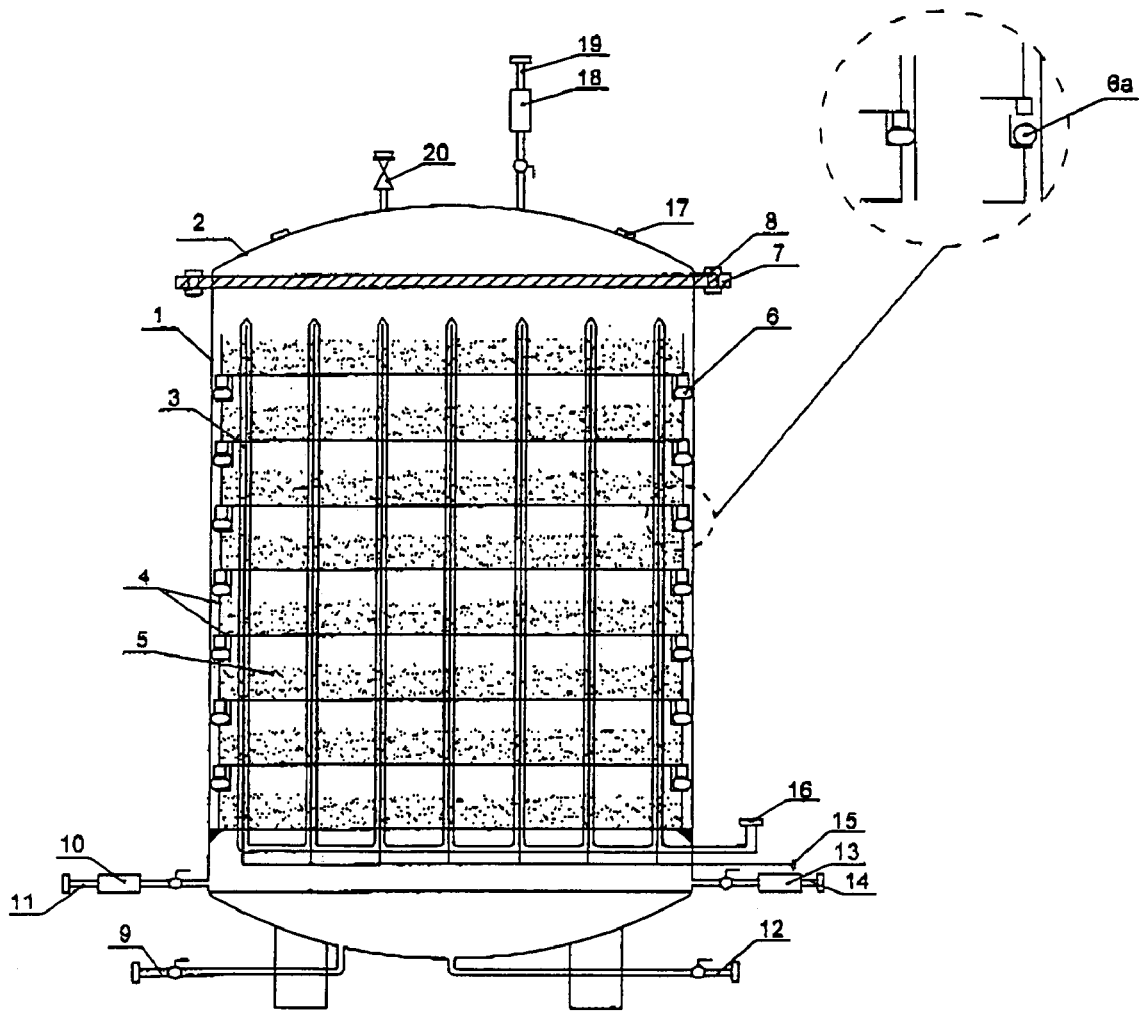
FIG. 1 (hereinafter "FIG. 1") illustrates a side plan view of a solid-state fermenter in accordance with the present disclosure.

As shown in FIG. 1, the cooling lances are connected underneath the lowest fermenter level with 2 tubes penetrating into the fermenter, one used for the feed and the other used for the return of the coolant. In this way, the outer wall of the fermenter, which is designed as a pressure vessel, need only be broken through at 2 places for the purpose of the cooling of the fermenter material.

The bases of the fermenter levels have been provided with holes. The holes have a diameter which is approx. 1 mm larger than the outer diameter of the cooling lances. They can be provided with lids which open in an upward direction, i.e. into the culture substrate. When fermenter levels are inserted into the fermenter from above, these lids are opened by the cooling lances and thus open the path for the same. Thanks to the circular cone shaped tip, the cooling lances can penetrate the culture substrate in the insertion of the fermenter levels into the fermenter without problems. As a result of the volume occupied by the cooling lances, a fermenter level may only be filled with culture substrate before insertion into the fermenter to such an extent that there is sufficient space in the fermenter level following insertion into the fermenter.

However, the filling of the fermenter levels can also be done after the level in question has been inserted into the fermenter in such a way that the level is just underneath the fermenter opening and the cooling lances have penetrated the base of the fermenter up to the intended height of the culture substrate. In this kind of filling, no lids are necessary to stop the holes in the fermenter levels. The levels are up to the intended height and inserted into the fermenter until they have contact to the fermenter base underneath.

In a special case, the described fermenter can be operated with only one level filled with the culture substrate. This is in particular possible if the granular culture substrate manifests a very stable structure and there is no risk that the culture substrate compresses during the sterilisation or the fermentation or alters its features in a different way to the detriment of the culture process.

2. Sealing of the Fermenter Levels to the Fermenter Wall

For the fermentation or culture of an aerobic micro-organism, a continuous feed of oxygen to the culture substrate on which the micro-organism develops is necessary. Therefore, air is guided through the culture substrate according to the invention claimed under WO 99/57239. However, this is only possible if the fermenter levels are sealed towards the walls of the fermenter. Otherwise, the air would flow past the levels due to the lower resistance and the culture substrate would not be sufficiently supplied with oxygen. A sealing of the fermenter levels towards the walls of the fermenter is additionally necessary for the inoculation of the fermenter. The inoculation is done according to the invention claimed under WO 99/57239 by the fermenter being banked to above the top fermenter level with sterile water. The inoculum, which distributes in the water, is then inserted via a hole in the lid. An even inoculation of all the fermenter levels is subsequently reached by the water being discharged from the fermenter again through a discharge in the base. In this way, there is an even flow through all the fermenter levels and simultaneous contamination with the inoculum. However, this is only possible if the water does not flow past the fermenter levels at the side.

The air-proof and waterproof seal is achieved in the invention by a seal which is installed between the fermenter levels and is pressed together by the mass of the level positioned above it (FIG. 1). The seal comprises an elastic, heat-stable material (e.g. silicone). When the seal is pushed together, it expands to the side and is pressed against the inner wall of the fermenter. This then ensures the necessary air-proof and waterproof lock. In order to prevent the seal from being pressed together too strongly, the upper fermenter level is positioned on the one underneath it. This can be achieved, for example, by spacers (FIG. 1), which result in the space for the seal pressed together being equal between all the levels. The seal can be installed either on the top edge of the lower level or on the edge below the base of the upper level, e.g. with the help of a groove.

Merely the lowest fermenter level, which is mainly used to accommodate a moistening medium, is positioned on a ring, which is firmly installed on the fermenter wall (FIG. 1) and on which a seal is positioned.

LIST OF REFERENCE SIGNS

Figure 2:
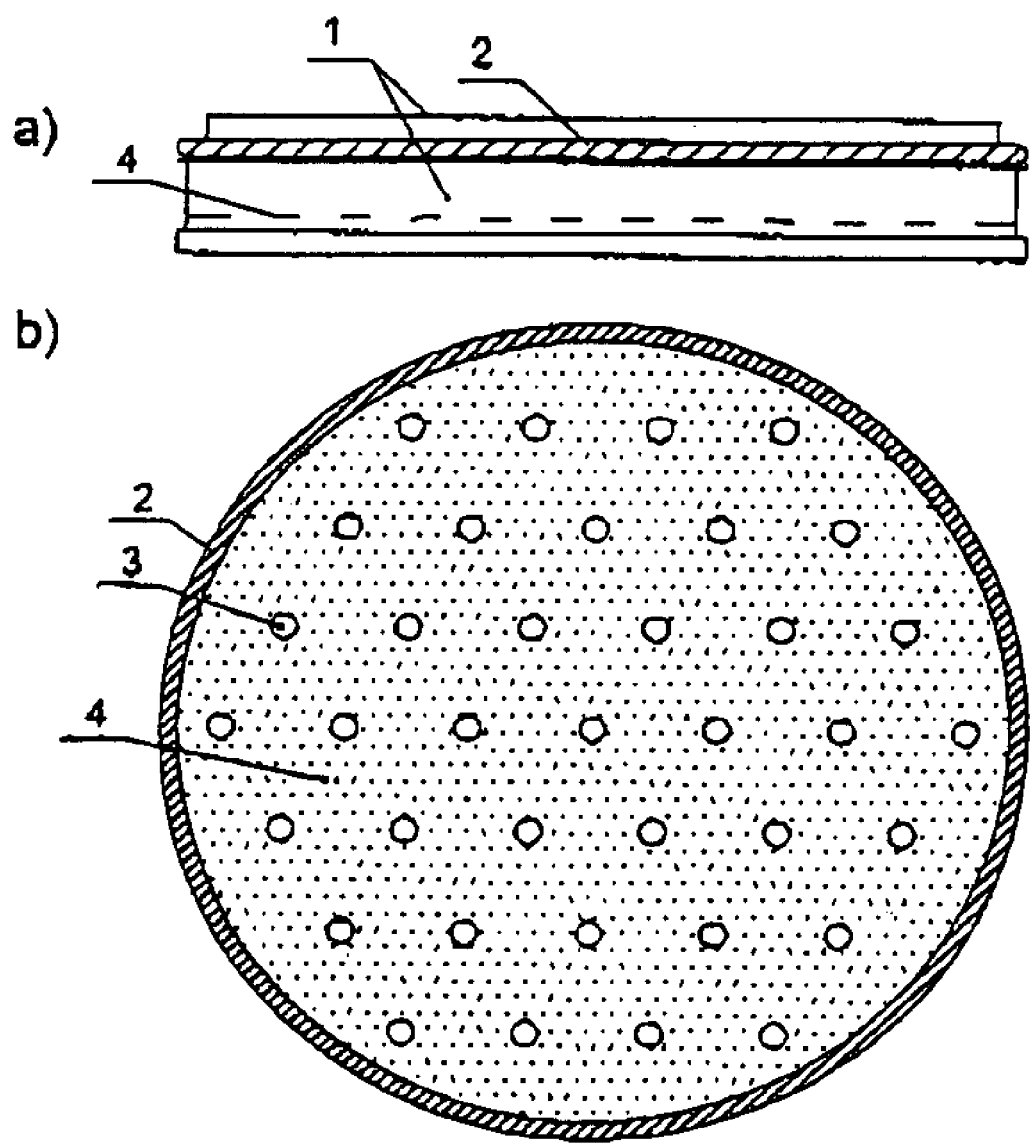
FIG. 2a (hereinafter "FIG. 2a") illustrates a front plan view of a fermenter level in accordance with the present disclosure.
FIG. 2b (hereinafter "FIG. 2b") illustrates a top plan view of the fermenter level of FIG. 2a in accordance with the present disclosure.
Figure 3:
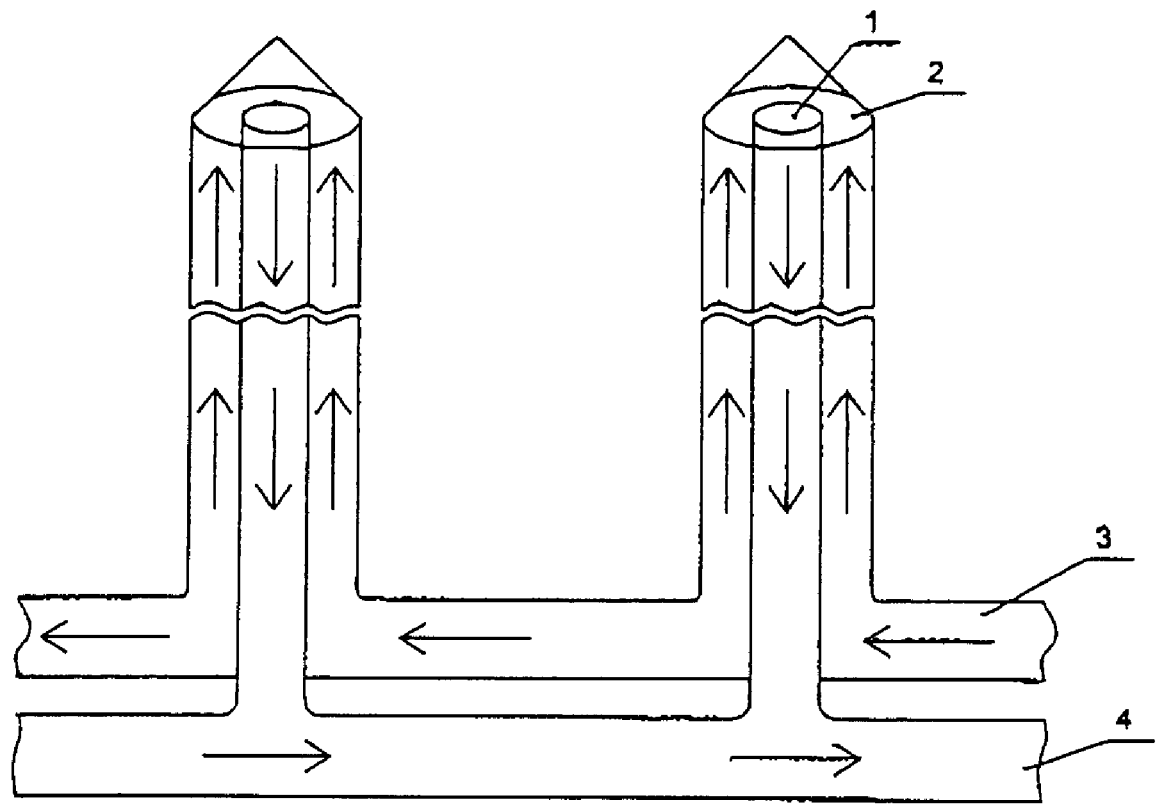
FIG. 3 (hereinafter "FIG. 3") illustrates a cross-sectional view of cooling lances in accordance with the present disclosure.

FIG. 1
1 Fermenter wall
2 Fermenter lid
3 Cooling lance
4 Fermenter level
5 Substrate for culture of micro-organisms
6 Seal between the fermenter levels
6a Relieved seal
7 Lid seal
8 Lid screw connection
9 Vapour inlet
10 Sterile water filter
11 Water inlet
12 Discharge
13 Sterile air filter
14 Air inlet
15 Coolant return
16 Coolant feed
17 Inoculation opening
18 Sterile exhaust air filter
19 Air discharge
20 Safety valve FIG. 2
a) Front view
B) Top view
1 Fermenter level wall
2 Seal
3 Openings for the cooling lances
4 Level bases, comprising perforated sheet FIG. 3
1 Internal tube
2 External tube
3 Feed
4 Return

The invention claimed is:

1. Solid-state fermenter comprising a plurality of air and water-permeable fermenter levels for accommodating a culture substrate arranged above one another and connected with an inner wall of the fermenter in such a way that neither air nor water can flow past the levels laterally,
cooling lances vertically rising from a fermenter base and leading through the fermenter levels via holes provided in the fermenter levels, and
a seal between each succeeding fermenter level, the seal being pressed against the inner wall of the fermenter by the weight of the level above it.

2. Solid-state fermenter according to claim 1, wherein the cooling lances are positioned in a triangular arrangement to one another and each cooling lance is equidistant to the other cooling lances immediately surrounding.

3. Solid-state fermenter according to claim 1, wherein each cooling lance comprises a first internal tube with a smaller diameter for return of coolant, and a second tube with a larger diameter for feed of coolant in which the first internal tube is concentrally arranged.

4. Solid-state fermenter according to claim 1, wherein the second tube has a circular cone shaped stopper at its upper end and an upper end of the first tube is located 1-2 cm below the stopper.

5. Solid-state fermenter according to claim 1, wherein each cooling lance has an outer diameter of 1-3 cm.

6. Solid-state fermenter according to claim 1, wherein the ratio of the diameters of the first and second tubes is designed in such a way that the flow velocity of coolant in feeding is equal to the flow velocity of coolant in the return.

7. Solid-state fermenter according to claim 1, wherein the seal comprises an elastic, heat-resistant material.

8. Solid-state fermenter according to claim 1, wherein the seal comprises silicone.

9. Solid-state fermenter according to claim 1, wherein spacers are arranged between the levels.

10. Solid-state fermenter according to claim 1, wherein the seal is installed either on an upper edge of a lower level or on an edge below a base of an upper level, within a groove.

11. Solid-state fermenter according to claim 1, wherein the bottom fermenter level is positioned on a ring firmly installed in the fermenter inner wall, a seal being positioned on the ring.

* * * * *